United States Patent [19]
Kolpe et al.

[11] Patent Number: 5,178,957
[45] Date of Patent: Jan. 12, 1993

[54] NOBLE METAL-POLYMER COMPOSITES AND FLEXIBLE THIN-FILM CONDUCTORS PREPARED THEREFROM

[75] Inventors: Vasant V. Kolpe, Mendota Heights; Paul M. Williams, St. Paul, both of Minn.

[73] Assignee: Minnesota Mining and Manufacturing Company, St. Paul, Minn.

[21] Appl. No.: 726,643

[22] Filed: Jul. 2, 1991

Related U.S. Application Data

[63] Continuation of Ser. No. 346,517, May 2, 1989, abandoned.

[51] Int. Cl.$^5$ .............................................. B32B 15/08
[52] U.S. Cl. .................................................. 428/458
[58] Field of Search ................... 428/457, 141, 458; 128/784

[56] References Cited

U.S. PATENT DOCUMENTS

| | | | |
|---|---|---|---|
| 4,568,598 | 2/1986 | Bilkadi et al. | 428/141 |
| 4,762,135 | 8/1988 | van der Puije et al. | 128/784 |

FOREIGN PATENT DOCUMENTS

| | | |
|---|---|---|
| 187706 | 7/1986 | European Pat. Off. |
| 265007 | 4/1988 | European Pat. Off. |
| 915518 | 1/1963 | United Kingdom |
| 1066839 | 4/1967 | United Kingdom |
| 1211669 | 11/1970 | United Kingdom |
| 1304072 | 1/1973 | United Kingdom |
| 1331491 | 9/1973 | United Kingdom |
| 1339157 | 11/1973 | United Kingdom |
| 1373790 | 11/1974 | United Kingdom |
| 1417628 | 12/1975 | United Kingdom |

OTHER PUBLICATIONS

White et al., Ann. N.Y. Acad. Sci., 405:183-190 (1983).
White, "System Design of a Cochlear Implant", IEEE Engineering in Medicine and Biology Magazine, vol. 6, No. 2, pp. 42-46 (1987).
Roberts et al., 2nd Quarterly Progress Report, Jan. 1, 1984 through Mar. 31, 1984, NIH Contract NO1-NS-3-2352.
"Multichannel Multiplexed Intracortical Recording Arrays", Quarterly Report #1 (Cont. NIH-NINC-DS-NO1-NS-7-2397) (Feb. 1988) pp. 1, 11-13.
VanDerPuije et al., "Cylindrical Cochlear Electrode Array for Use in Humans", Ann. Otol. Rhinol. Laryngol., 98:466-471 (1989).
Sonn, M. and W. Feist, 1974, A Prototype Flexible Microelectrode Array for Implant-Prosthesis Applications: Med. Biol. Eng.:778.
Clark, G. M. and R. J. Hallworth, 1976, J. Laryngol. Otol. 90:623.
Shamma-Donoghue, Shihab A., G. A. May, N. E. Cotter, R. L. White and F. B. Simmons, 1982, Thin-Film Multielectrode Arrays for a Cochlear Prosthesis, IEEE Trans. Elect. Devices (ED-29)1:136-144.

Primary Examiner—Thomas J. Herbert, Jr.
Attorney, Agent, or Firm—Gary L. Griswold; Walter N. Kirn; Paul W. Busse

[57] ABSTRACT

A composite article is prepared as a polymeric support having a coating of noble metal deposited on at least one surface thereof, the coating exhibiting suitable peel force for high performance applications such as the preparation of an electrode, such as a biocompatible, flexible, thin-film microelectrode where in the composite article can be prepared by pretreating at least one surface of the support by sputter etching, followed by sputter-depositing a noble metal on the pretreated surface in order to form the coating of noble metal.

13 Claims, 5 Drawing Sheets

NOBLE METAL-POLYMER COMPOSITES AND FLEXIBLE THIN-FILM CONDUCTORS PREPARED THEREFROM

This is a continuation of application Ser. No. 07/346,517 filed May 2, 1989 now abandoned.

TECHNICAL FIELD

The present invention relates to composite articles made of noble metals deposited on thin, flexible polymeric supports, and the use of such articles for diverse, high performance applications, such as the fabrication of electrodes for use in biological environments. In another aspect, the present invention relates to composite articles useful for the fabrication of biocompatible, flexible, thin-film microelectrodes of special utility as stimulating multiconductor, multichannel bioelectrodes, e.g., cochlear implant electrodes; to methods of preparing such articles and of fabricating such electrodes; and to the articles and electrodes themselves.

BACKGROUND ART

The fabrication of electrodes for biological applications such as neural stimulation has gained increased attention in recent years. Biocompatible (e.g., implantable), flexible, thin-film, multiconductor microelectrode stimulation arrays have been investigated for use as, inter alia, complex neural prostheses, such as cochlear prostheses. See, e.g., White, et.al., *Ann. N.Y. Acad. Sci*, 405:183-190 (1983). This article describes some of the technological difficulties inherent in fabricating thin-film neurostimulating arrays. Such difficulties arise not because of an inability to control, by photolithographic technology, the dimensional resolution of the arrays, but rather because of the inability of the art to fabricate the stable, flexible and durable composite (e.g., metal-polymer) materials necessary for preparing such arrays.

For example, multiple conductor miniature electrodes that are used for stimulating the residual nerve fibers of an impaired human cochlea or inner ear are subjected to demanding clinical conditions. They require long-term reliability and stability of the metal-polymer interface, as well as the ability to provide a suitable charge transfer from stimulating electrodes having geometrically small surface areas.

It is desirable that such electrodes would ideally be made up of both a noble metal conductor, such as platinum, and a polymeric support, such as polyimide. Both of these materials are presumed to be biocompatible, and are known to be bioinert. This very inertness however makes it extremely difficult to attach the two materials directly to each other in a manner that will enable the resulting composite to undergo conventional photolithography, as well as to then withstand the rigors of a biological environment. The authors of the above White et.al. article recognized this problem, and attempted to solve it by the use of a thin intermediate layer of tantalum or titanium between the surface of the polymer substrate and the platinum layer. Delamination of platinum from the polyimide substrate continued to be a vexing problem however, see e.g., White, "System Design of a Cochlear Implant", *IEEE Engineering in Medicine and Biology Magazine*, Vol. 6, No. 2, pp. 42-46 (1987).

Other authors have similarly expressed the frustration and difficulty of this problem. For instance, Roberts et.al., 2nd Quarterly Progress Report, Jan. 1, 1984 through Mar. 31, 1984, NIH Contract N01-NS-3-2352, states that "[m]etal to polyimide adhesion after electrical stimulation continues to be a difficult and elusive property to achieve." This report comments on how a composite can appear to exhibit good adhesion under a saline soak test, but fail as soon as electrical stimulation is applied. Since such conditions are used to simulate those encountered in biological applications, this report illustrates the need to fabricate flexible thin-film composite articles that are suitable for preparing electrodes for use in such biological environments and other demanding applications.

Researchers at the solid state Electronics Laboratory of the Bioelectrical Sciences Laboratory, University of Michigan, have explored the development of polyimide-tantalum thin film conductor cables. Adhesion of metals to polyimide, and saline durability, are described as major problems. "Multichannel Multiplexed Intracortical Recording Arrays", Quarterly Report #1, (Contract NIH-NINCDS-N01-NS-7-2397) (February 1988).

SUMMARY OF THE INVENTION

The present invention provides a composite article useful for diverse high performance applications, including the preparation of electrodes, such as biocompatible, flexible, thin-film microelectrodes. The article of the present invention comprises a polymeric support having a coating of a noble metal deposited on at least one surface thereof, the coating exhibiting suitable peel force for use in high performance applications.

According to test method(s) explained more fully below, the noble metal coating of preferred articles of the invention exhibits a suitable peel force for its intended purposes, e.g., a peel force of at least about 0.05 kg per millimeter width after 24 hour boiling saline treatment.

Preferably the coating is a continuous coating and further exhibits (1) sheet resistance of about 3 ohms per square or less before boiling saline treatment, and (2) sheet resistance of about 9 ohms per square or less after boiling saline treatment.

The invention further provides a method for making such an article, which method comprises the steps of (a) pretreating at least one surface of a polymeric support by sputter-etching, and (b) sputter-depositing a noble metal on the pretreated surface in order to form a coating of the noble metal. Preferred articles of this invention can be subjected to conventional microelectronic photolithographic techniques in order to provide electrodes that exhibit suitable quality, electrical performance, and durability under demanding conditions.

BRIEF DESCRIPTION OF THE DRAWING

A more complete understanding of the invention and its advantages will be apparent from the Detailed Description taken in conjunction with the accompanying Drawing, in which.

DETAILED DESCRIPTION

Figure 1:
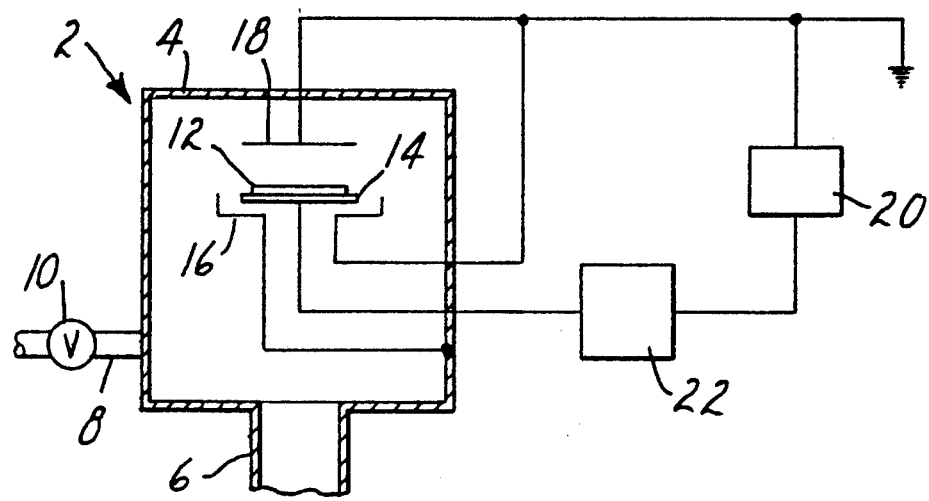
FIG. 1 illustrates a schematic view of a typical sputter etching device.

The present invention provides composite articles comprising a noble metal coating on a polymeric support, as well a method of preparing such composite articles, and finished articles, such as electrodes, fabricated from such composite articles.

A composite article of the present invention can be prepared as a polymeric support, at least one surface of the support having been pretreated by sputter-etching, the support thereafter having a coating of a noble metal sputter-deposited on the pretreated surface. By pretreating the support in the manner described in the present invention, it is possible to deposit a noble metal in a manner that provides suitable continuity and adherence of the metal to the support. The resultant composite article is well-suited for the fabrication of finished articles, e.g., electrodes for use under demanding conditions.

The word "pretreat", and inflections thereof, as used herein refers to the treatment of a polymeric surface, as by sputter-etching, in order to substantially improve the interfacial adhesion of the surface to a sputter-deposited noble metal. The word "substantially" as used in this sense means a degree of improvement that renders a previously unusable surface usable in the method of this invention for preparing composite articles having the properties described herein.

The preferred pretreatment of the method of the invention involves sputter-etching of a surface of the support. Conventional sputter-etching techniques can be applied to the method of the present invention. For example, suitable techniques are described in U.S. Pat. Nos. 4,155,826, 4,454,186, 4,481,234, and 4,568,598, the disclosures of each of which are hereby incorporated by reference. The term "sputter-etching" as used herein refers to the one-step or multi-step bombardment of a surface with neutral species and/or ions, e.g., oxygen, argon, carbon dioxide, nitrogen, or helium ions; this term includes ion beam milling as well as radio-frequency (RF) sputtering, and includes the deposition of trace quantities of elements, e.g., chromium as the oxide, on the inert polymer surface, as described, e.g., in U.S. Pat. No. 4,481,234.

In the sputter-etching pretreatment of the invention, the polymeric support preferably is specially prepared prior to being subjected to sputter-etching, in order to increase the effectiveness of the pretreatment and the resultant integrity of the coating of metal. Such preparation includes, for instance, the steps of (1) washing the support surface with appropriate cleaning agents in order to remove oils and particulates, and (2) thermally conditioning the washed support surface in order to reduce volatile contaminants and adsorbed water.

Cleaning agents suitable for use in preparing such supports include those that provide suitable compatibility with the support itself as well as effective removal of oils and particulates. Examples of suitable cleaning agents are known to those skilled in the art, and include organic solvents, such as heptane, isopropanol, and toluene and/or fluorocarbon solvents.

Drying of the support can be accomplished in a variety of ways that are compatible with supports of this sort. Preferably the support is dried by heating it in a manner that retains the dimensional and compositional integrity of the support, yet substantially ensures the absence of surface-absorbed water and volatile low molecular weight contaminants to an extent that the support can be effectively sputter-deposited. For instance, heating for about one to about three hours at temperatures approaching but sufficiently below the softening point to avoid softening of the support is generally sufficient. For example, for "Kapton TM" polyimide film, direct or programmed (i.e., incremental) heating to approximately 180° C., and holding at this temperature for a period typically on the order of about two hours, is generally sufficient.

Supports that need to be stored after preparation and before sputter-etching, can be stored in a manner that avoids recontamination of the prepared surface, e.g., in sealed containers. Prior to sputter-etching, prepared surfaces are preferably passed under a stream of ionized gas (e.g., nitrogen) to remove any particles that may have become bound to the surface by electrostatic forces.

After preparation, the support can be subjected to sputter-etching using a conventional sputtering apparatus. Referring to FIG. 1 a schematic view of a typical sputter etching device is illustrated. The sputter etching device 2 includes an enclosure 4 which is gas tight. The atmosphere within enclosure 4 can be withdrawn through a vacuum pump attached to exhaust pipe 6, or supplemented through the gas inlet pipe 8, controlled by the gas inlet valve 10. The workpiece 12 which is to be etched is placed on a cathode 14, which is partially surrounded by a shield electrode 16. Suspended above the cathode 14 is an anode 18. The chamber walls of enclosure 4 are anodic as well. Alternating current is applied to these electrodes by an RF power supply 20, conditioned by RF impedance matching circuitry 22.

The surface of the support is sputter-etched to an extent that will provide the desired adherence to a sputter-deposited noble metal. The word "surface" as used herein refers to the outer molecular layers of the support, and in particular, to that depth of a polymeric sheet surface that, when pretreated, yields a structure, e.g., peak-to-valley ratio, that substantially improves adhesion to a sputter-deposited noble metal.

In a preferred embodiment of the present invention, e.g., in which the polymeric support is polyimide, sputter etching is generally carried out using a discharge power of between about 0.05 to about 0.25 watts/square centimeter, in a Perkin-Elmer discharge chamber having a cathode area of 1940 square centimeters. Typically, the gas pressure inside the evacuated chamber is lowered to between about $8 \times 10^{-5}$ torr to $4 \times 10^{-4}$ torr. Oxygen gas is then admitted at 20 standard cubic centimeters per minute ("SCCM") in order to maintain the chamber pressure at about $6 \times 10^{-3}$ torr during sputter-etching. The voltage drop across the electrodes is about 0.05 to about 1 KV, at a standard frequency of about 13 to about 15 MHz. Under such conditions, the polyimide is sputter-etched for between about one-half and about 10 minutes, and preferably between about 4 and about 6 minutes in order to achieve a suitable pretreatment.

As a result of sputter-etching, the pretreated surface surprisingly exhibits improved adherence to a sputter-deposited noble metal, and in turn the resulting composite exhibits suitable adherence between the surface and the coating of noble metal.

While noble metal can be deposited on a pretreated surface by a variety of metal deposition techniques, sputter-deposition of noble metal is preferred.

The term "sputter-deposit", as used herein, refers to a process or technique of depositing metal by means of a sputter plasma onto an object to be coated with the metal. The process generally involves the one-step bombardment of a noble metal target with energetic neutral species and ions which results in the transfer of kinetic energy to atoms of the metal, which in turn are ejected from the target and collide with the surface that is to receive the metal deposit. Suitable metal deposition techniques include those described, e.g., in U.S. Pat. Nos. 4,454,186, 4,568,598 and 4,481,234. In order to ensure optimum results, sputter-deposition of the noble metal is preferably carried out without any intervening exposure of the pre-treated surface to ambient conditions, e.g., exposure to air.

Preferably the metal is deposited on the pretreated support in a manner analogous to that described in *Thin Film Processes*, "Glow Discharge Sputter Deposition", Chapter 2, pp. 12-62, J.L. Vossen et.al., eds. Academic Press, New York, N.Y. (1978), the disclosure of which is hereby incorporated by reference. In particular such methods involve sputter-deposition using neutral atom bombardment of a noble metal cathode.

The word "coating", as used herein, refers to the layer of noble metal obtained on a pretreated surface, e.g., by sputter-deposition. The coating preferably is continuous, i.e., it has (at least within an area of a size suitable for its intended use) substantially no visible pin holes or cracks therein, and exhibits suitable continuity for its intended purpose, e.g., it exhibits a sheet resistance suitable to allow the use of the area as a path for electrical current.

Suitable composites are those exhibiting the qualities, e.g., continuity of the metal layer, stability, and durability, necessary for their intended use, e.g., as bioelectrodes. Such qualities can be evaluated by a variety of means, including visual inspection, peel force tests, and saline soak tests, specific examples of each of which are described in greater detail below.

According to Test Method A explained more fully below, the noble metal coating of a preferred article of the invention exhibits a suitable peel force for its intended purposes, e.g., a peel force of at least about 0.05 kg per millimeter width after 24 hour boiling saline treatment.

Preferred are articles that exhibit a peel force of at least about 0.1 kg/mm, and particularly preferred are articles that exhibit a peel force of at least about 0.15 kg/mm.

Preferably the coating is a continuous coating and further exhibits (1) sheet resistance of about 3 ohms per square or less before boiling saline treatment, and (2) sheet resistance of about 9 ohms per square or less after boiling saline treatment.

When the article is going to be used in electrical applications, particularly preferred is a continuous coating that exhibits sheet resistance of about 2 ohms per square or less before boiling saline treatment, and about 5 ohms or less per square after boiling saline treatment according to Test Method B. Most preferred is a coating that exhibits sheet resistance of about 1 ohm per square or less before boiling saline treatment and about 3 ohms or less per square after boiling saline treatment.

Figure 2:
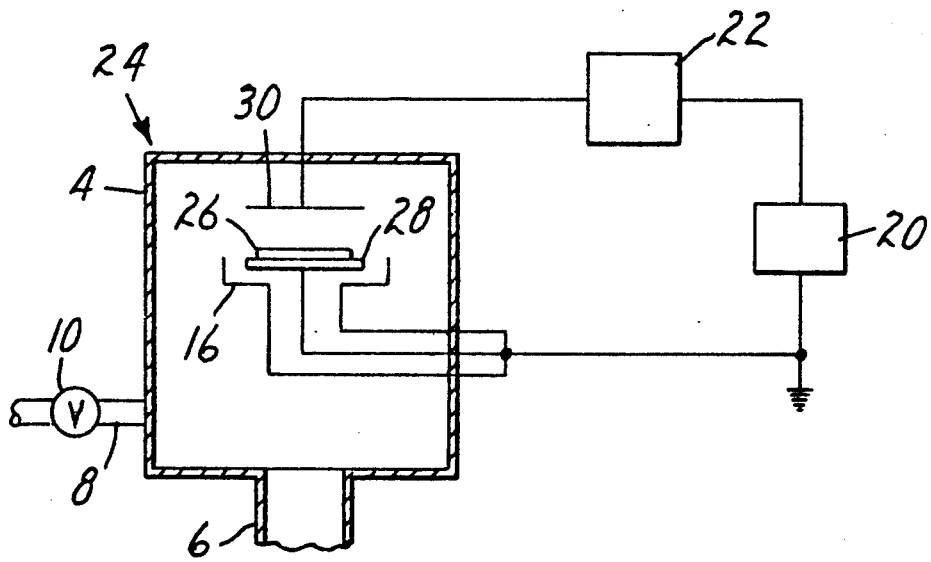
FIG. 2 illustrates a schematic view of a typical sputter deposition device.

Referring to FIG. 2 a schematic view of a typical sputter deposition device is illustrated. The sputter deposition device 24 also includes an enclosure 4 which is gas tight. The atmosphere within enclosure 4 can be withdrawn through a vacuum pump attached to exhaust pipe 6, or supplemented through the gas inlet pipe 8, controlled by the gas inlet valve 10. The workpiece 26 on which material is to be deposited is placed on an anode 28, which is partially surrounded by a shield electrode 16. Suspended above the anode 28 is a noble metal cathode 30. Alternating current is applied to these electrodes by an RF power supply 20, conditioned by RF impedance matching circuitry 22.

Figure 3:
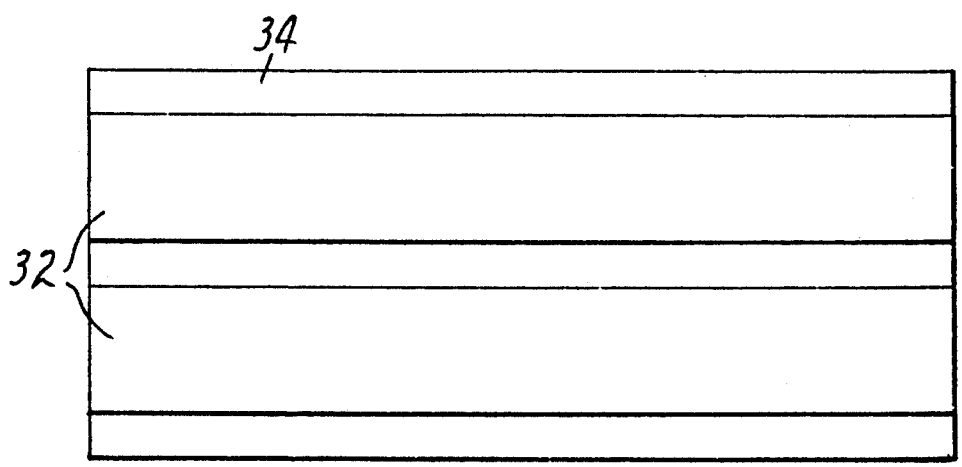
FIG. 3 illustrates a test surface bearing a noble metal coating in two strips on a pretreated polymeric support according to the present invention.

Referring to FIG. 3, a test surface bearing a noble metal coating on a pretreated polymeric support according to the present invention is illustrated. Strips of noble metal 32 have been sputter deposited on the polymeric support 34 which has been pretreated according to the method of the present invention.

Figure 4:
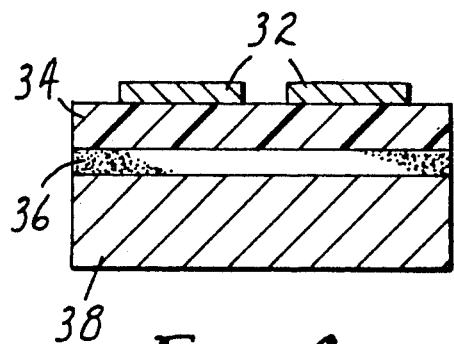
FIG. 4 illustrates a cross section of the test surface of FIG. 3.

Referring to FIG. 4, a cross section of the test surface of FIG. 3 is illustrated. The strips of noble metal 32 are seen deposited on the pretreated polymeric support 34. The polymeric support 34 is shown adhered by a layer of pressure sensitive adhesive 36 to a stiff backing 38.

Suitable materials for the preparation of the composite articles of this invention, i.e., suitable polymeric supports and noble metals, can be identified as described below.

Suitable polymeric supports for use in the present invention exhibit an optimal combination of such properties as inertness, optical transmissiveness, and stability during processing, e.g., the surface of such supports should not soften or melt during sputter-etching. Such supports also possess negligible amounts of contaminants that could migrate to the surface after sputter-etching, thereby destroying the effectiveness of the pretreatment. Examples of suitable polymeric supports include polyimide films, such as Kapton TM, Kapton-H TM, and "Pyralin TM PI 2555", each available from E.I. DuPont de Nemours and Company, Wilmington, Del., "Kaneka" TM polyimide film available from Kanegafuchi Chemical Industries Co., Ltd., Osaka Japan, and Upilex TM polyimide film, available from UBE Industries, Ltd., Tokyo, Japan. Other suitable polymeric supports include, but are not limited to, polyester films, polyethylene terephthalate, and films prepared according to known techniques from polyester-ether block copolymers such as polybutylene terephthalate-polytetramethylene etherglycol terephthalate resins, e.g., those available as the "Hytrel" TM resins from E.I. DuPont de Nemours, Inc., Wilmington, Del.

Preferred polymeric supports for use in the present invention are in the form of sheets, e.g., films or tapes, and exhibit an optimal combination of such properties as wide temperature range stability, high decomposition temperature, and the ability to resist undesired chemical or physical changes during the method of the present invention. Thermoset polyimide sheet supports are generally preferred in view of their widespread acceptance in the field of implantable electrodes and their ability to provide a suitable combination of the above properties.

Examples of preferred polymeric supports include polyimide tape, e.g., "Kapton TM" tape available from 3M Company as No. 5413 tape, and polyimide film available from DuPont as "Kapton-H TM" film. Other preferred polymeric sheet supports include films prepared from "Hytrel" TM block copolymers such as "Hytrel 6098", such resins available from DuPont.

The term "noble metal", as used herein, refers to a metal that is not readily oxidized. (See, e.g., Grant & Hackh's Chemical Dictionary, McGraw-Hill Book Co., New York, N.Y., 4th Ed., 1987). Suitable metals for use in the composites of the present invention are the noble metals, gold, iridium, palladium, platinum, rhodium, ruthenium, and their alloys. When used in biological applications, suitable metals exhibit a desired degree of conductivity, and biocompatibility (e.g., neurocompatibility). Preferred noble metals are exemplified by platinum and its alloys and iridium and its alloys. While gold has not found wide use in bioelectrodes, particularly for "above the neck" neurostimulation human implants, gold is suitable for use in other applications of the composite articles of this invention, e.g., for use in functional neuromuscular stimulation.

Particularly preferred noble metals for biological applications are those that are bioinert when used as an electrical charge carrier in proximity to biological tissues, and that exhibit an optimal combination of such properties as adherence to the pretreated polymeric sheet support, conductivity, cost, and reproducibility and ease of use in sputter-deposition.

An example of a particularly preferred noble metal for use in implantable bioelectrodes is platinum, for example, 99.99% pure platinum target, such as that available from Varian Associates, Inc., Specialty Metals Division, Grove City, Ohio.

Following metal deposition, the resulting composite articles can be used for a variety of applications, e.g., as neural stimulating electrodes, neuromuscular stimulating electrodes, biosensors, and the like. For use as stimulating electrodes, the articles will generally be subjected to photolithography, e.g., microelectronic photolithography, in order to fabricate a multicomponent microelectrode stimulation array. The word "fabricate" and inflections thereof, as used herein refers to the method(s) used to prepare a device or other useful article, e.g., an electrode, from a composite article of this invention. Conventional photolithographic techniques can be used for fabricating such arrays, and will not be repeated here. Representative techniques are described, for instance, in Elliot, *Integrated Circuit Fabrication Technology*, McGraw Hill Co., 1982, the disclosure of which is hereby incorporated by reference.

Figure 5:
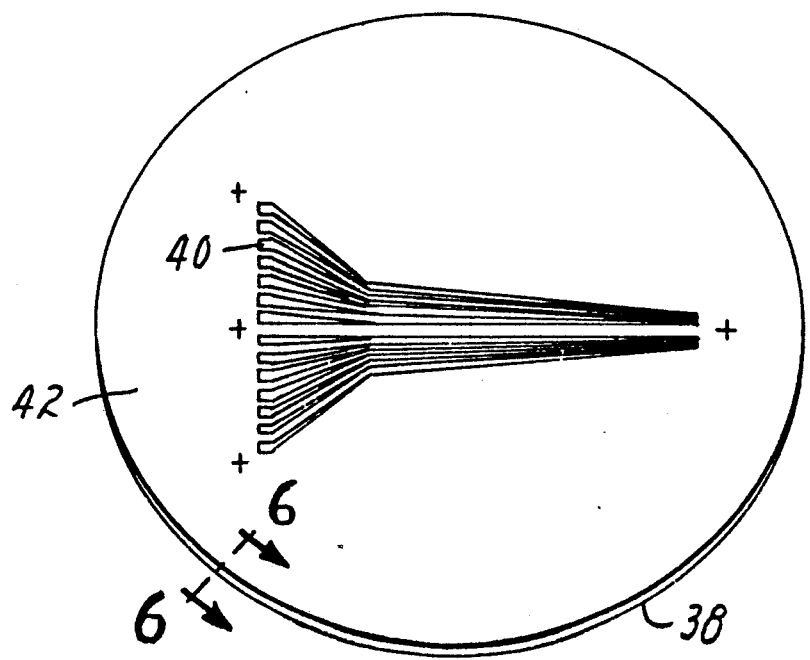
FIG. 5 illustrates a perspective view of a stage in the construction of a single sided electrode array.

Referring to FIG. 5, a perspective view of the penultimate stage in the construction of a single sided electrode array, just before the array is cut from the film, is illustrated. The conduction paths 40 fashioned of noble metal on a polymeric support using photolithographic methods are seen. The exact dimensions of the array vary depending on the physiology of the recipient, so no general dimensions are given.

Figure 6:
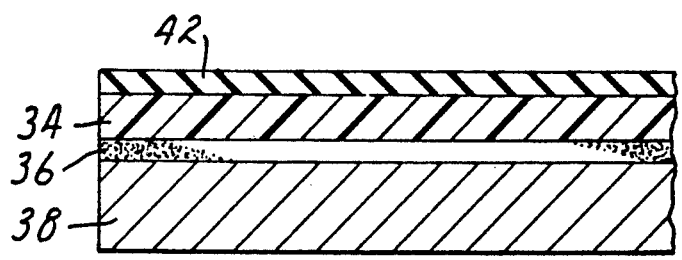
FIG. 6 is an enlarged sectional view taken along line 6—6 of FIG. 5.

FIG. 6 depicts the layer structure at the edge of the construction illustrated in FIG. 5. Onto a stiff backing 38, a polymeric support 34 is shown adhered by a layer of pressure sensitive adhesive 36. The layer of adhesive is an optional feature which can be dispensed with in the making of this structure by, for example, binding the polymeric support 34 to the stiff backing 38 by an annulus of adhesive tape. An insulative layer 42 covers the upper layer of the polymeric sheet support 34 at this point in the fabrication.

Figure 7A:
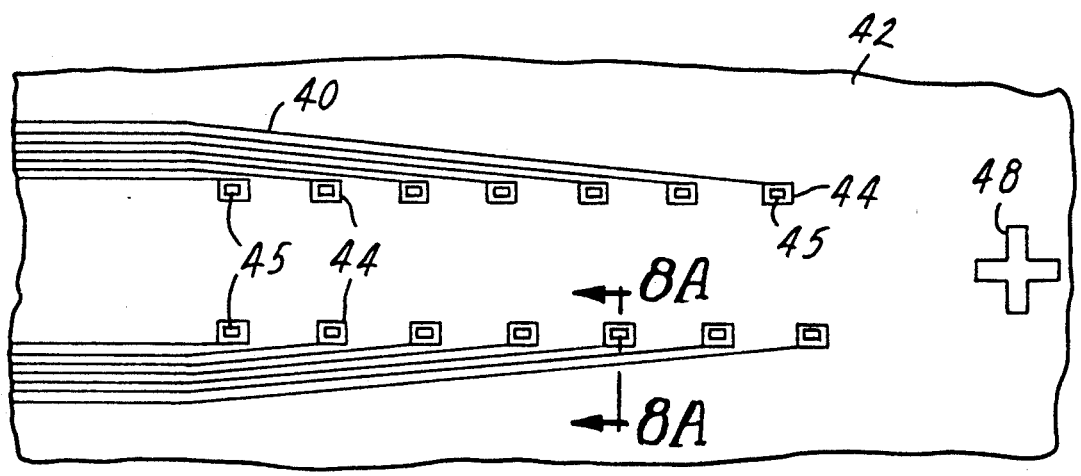
FIG. 7A is an enlarged fragmentary view of FIG. 5, and points out the fine structure of the right end of the array in a variation of the invention.

FIG. 7A depicts the fine structure of the end of an array in a variation of the invention. The conduction paths 40 are seen through the transparent insulative layer 42. Each conduction path 40 terminates in a pad 44, which delivers current to the external environment through a window 45 in the insulative layer 42. Also shown is alignment mark 48.

Figure 7B:
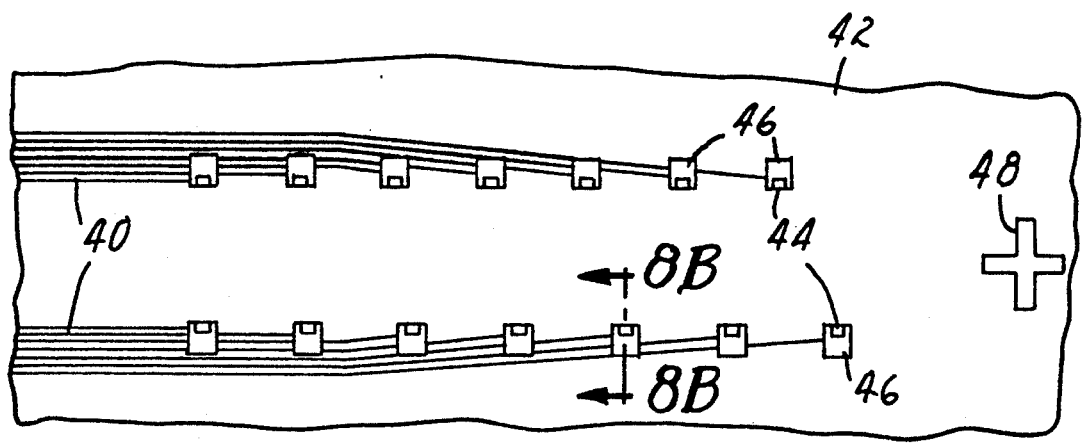
FIG. 7B is a view similar to 7A illustrating an alternative variation of the invention.

FIG. 7B depicts the fine structure of the end of an array in an alternative variation. The conduction paths 40 are seen through the transparent insulative layer 42. Each conduction path 40 terminates in a pad 44, which delivers current to the external environment through a stimulating plate 46 which extends through a window 45 in the insulative layer 42.

Figure 8A:
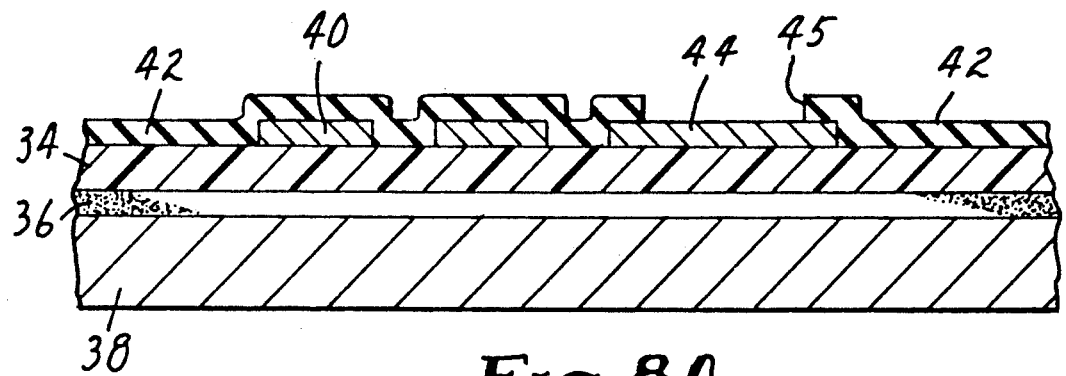
FIG. 8A illustrates a cross section view cut along section lines 8A—8A in FIG. 7A.

Referring to FIG. 8A, a cross section view cut along section lines 8A—8A in FIG. 7A is illustrated. The conduction paths 40 are seen end on, running along and deposited on the polymeric support 34. The insulative layer 42 protects the flow of current within the conduction paths 40 except where they terminate in a pad 44. Here, the insulative layer has been removed over a section of the pad 44, creating a window 45 through which the pad 44 is in electrical contact with the external environment.

Figure 8B:
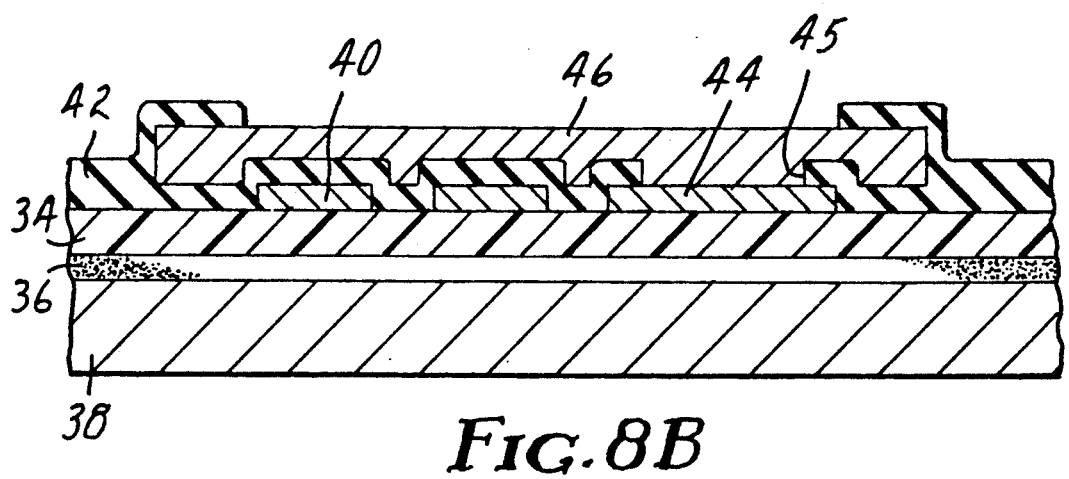
FIG. 8B illustrates a cross section view cut along section lines 8B—8B in FIG. 7B.

Referring to FIG. 8B, a cross section view cut along section lines 8B—8B in FIG. 7B is illustrated. In this view, an additional layer of platinum is deposited to form the stimulating plates 46, and additional insulative material is deposited covering the edges of the stimulating plates 46. This additional insulative material merges with the previously laid down insulative layer 42. The conduction paths 40 are seen end on, running along and deposited on the polymeric substrate 34. The insulative layer 42 protects the flow of current within the conduction paths 40 except where they terminate in a pad 44. Here, the insulative layer has been removed, forming a window 45. Above the window 45 additional conductive material is deposited forming a stimulating plate 46, which is in electrical contact with the pad 44 and with the external environment.

Figure 9:
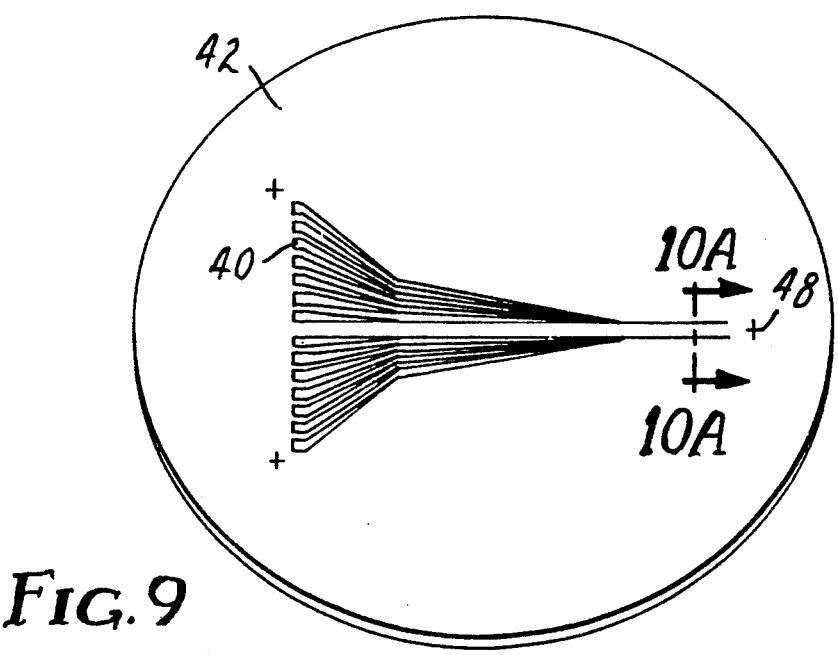
FIG. 9 illustrates a perspective view of an intermediate step in the fabrication of a two sided electrode array demonstrating the use of viewing ports for aligning the photolithographic masks on the far side.

Referring to FIG. 9, a perspective view of an intermediate step in the fabrication of a two-sided electrode array is illustrated. A single sided array is fabricated on one side of a flexible backing. On the opposite side is deposited a layer of noble metal from which the second array will be prepared. Viewing ports for aligning the photolithographic masks are left on the far side by the simple expedient of covering small regions on the far side opposite the alignment marks on the near side with a bit of adhesive tape during the deposition step. Several of these alignment marks 48 can be seen in this view.

Figure 10A:
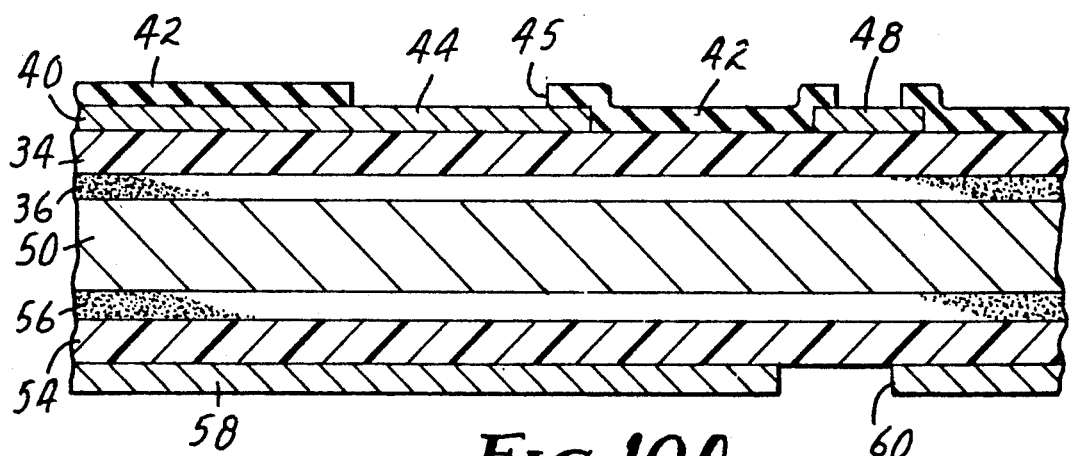
FIG. 10A is an enlarged cross section view taken along lines 10A—10A in FIG. 9.

Referring to FIG. 10A, a cross section view cut along section lines 10A—10A in FIG. 9 is illustrated. The structure is shown having a flexible backing 50, which in turn has two layers of polymeric support 34 and 54 adhered to its two sides by two layers of pressure sensitive adhesive 36 and 56. On one side, the elements of the above-described single sided array, i.e., the conduction paths 40, the insulative layer 42, and the pads 44 exposed through windows 45, have been fabricated. On the opposite side of the flexible backing 50, a second coating of noble metal 58 has been deposited to allow the fabrication of a second set of conduction paths. A viewing port 60 has been left uncovered by metal so that the alignment mark 48 on the first side can be seen through the various translucent layers, allowing coordinated placement of the conduction paths on both sides of the flexible backing.

Figure 10B:
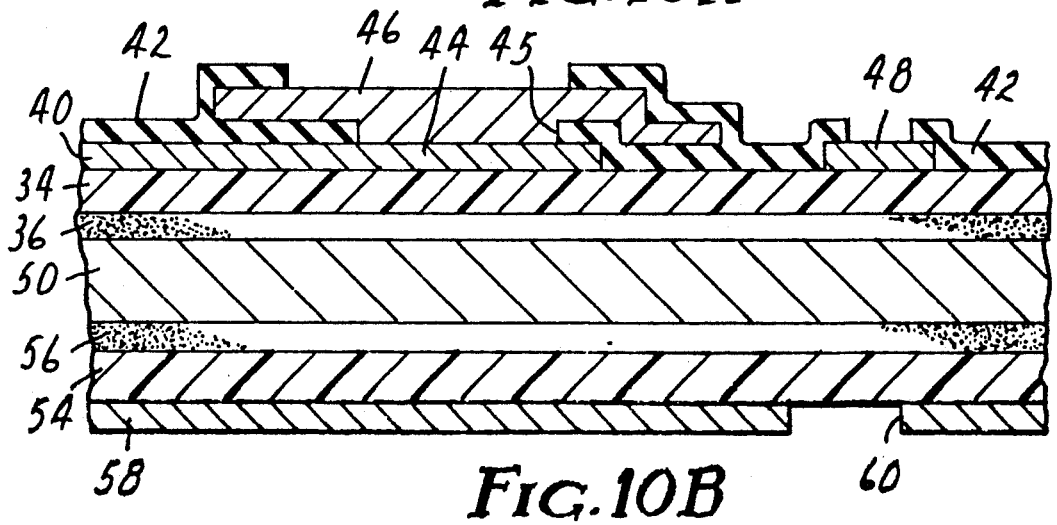
FIG. 10B is a view similar to FIG. 10A showing a variation of the invention.

Referring to FIG. 10B, a cross section view cut along section lines 10A—10A in FIG. 9 of a variation of the invention analogous to FIG. 8B is illustrated. As in FIG. 10A, the structure is shown having a flexible backing 50, which has two layers of polymeric support 34 and 54 adhered to its two sides by two layers of pressure sensitive adhesive 36 and 56. On one side, the elements of the above described single sided array, the conduction paths 40, the insulative layer 42, the pads 44, and the stimulating plates 46 which contact the pads 44 through the windows 45 in the insulative layer 42 have been fabricated. On the opposite side of the flexible backing 50, a second coating of noble metal 58 has been deposited to allow the fabrication of a second set of conduction paths. A viewing port 60 has been left uncovered by metal so that the alignment mark 48 on the first side can be seen through the various translucent layers, allowing coordinated placement of the conduction paths on both sides of the flexible backing.

Those skilled in the art will recognize the applicability of articles of the present invention for a variety of other applications as well. For instance, in view of the improved adherence between the metal and the support, such articles can be used as films, multiple conductor flexible cables, catalytic metal supported on high performance polymer films, sensors (such as biosensors), passive electrical elements (such as inductors, capacitors, resistors, connector contacts and the like), or components of such elements, as well as stimulators.

The invention is further illustrated by the following EXAMPLES, but the particular materials and amounts thereof recited in these examples, as well as other conditions and details, should not be construed to unduly limit this invention.

EXAMPLES

Test Method A: Peel Force

A 5000 ml Pyrex reaction flask having one ground glass port connected to a borosilicate condenser was used. Ground glass joints were sealed with silicone grease (High Vacuum Grease, Dow Corning, Midland, Mich.). A conventional external heater or heating mantle was used to maintain a solution temperature of 100+/−2° C. All internal surfaces of glassware were cleaned using detergent solution followed by rinsing with water which was of at least 5 Megohm-cm resistivity. A saline solution was prepared by combining high purity water of at least 5 Megohm-cm resistivity with reagent grade NaCl compound to obtain a 0.154 molar (0.9% NaCl by weight) NaCl solution.

A volume of the saline solution sufficient to immerse all test materials in the glassware vessel was used. The specimens were placed into the vessel for a period of 24 hours at 100° C. Within three minutes after removal from the saline, specimens were rinsed with water of at least 5 Megohm-cm resistivity at a temperature of at least 23° C. but not greater than 100° C. Care was taken to ensure that the force of the rinse water was not sufficient to itself dislodge metal from the specimen surface. The wet specimens were briefly rinsed with isopropanol and allowed to dry under ambient conditions for 15 minutes.

A testing machine having tensile testing capabilities was used (Materials Testing System "No. 810.05", MTS Systems, Corp., Eden Prairie, Minn.), having a movable member that could be operated at constant rates of speed in the range of 0.5 to 5000 cm/min. (0.2-1968 in./min.) and an electronic load cell to simultaneously measure dynamic forces in the range of 0 to 22.4 kilograms (0 to 50 lbs). Also a high speed, single event recording storage oscilloscope was used which was capable of recording the peel force signal from the load cell, and transmitting the recorded signal to a printing machine.

A test tape was used having an adhesive coating of about 76 microns (0.0030 in.) adhered to a polyester tape backing having a thickness of about 130 microns (0.0050 in.) ("No. 56 tape", 3M Electrical Products Division, St. Paul, Minn.). Each 2.54 cm (1.0 in.) wide test tape was cut to a minimum length of 43.18 cm (17.0 in.) and gently laid onto an exposed 2.54 cm (1.0 in.)×20.32 cm (8 in.) subregion of a specimen. Four passes (1 second/pass) were made over each test tape with the roller previously described. A piece of test tape (approximately 27.94 cm (11.0 in.) long) was adhered to the portion of test tape not covering specimen, so as to cover up the tacky adhesive portion. Each test tape-specimen-test panel sample was heated at 130+/−2° C. for 2 hours in an oven, in order to enhance the bond strength, and allowed to cool at ambient temperature for one-half hour.

Peel force was evaluated as described below according to ASTM Test Method D903-49, Section 8 Paragraph 1, the disclosure of which is incorporated herein by reference. At room temperature (22+/−3° C.), two clamping fixtures, one fixed and the other mounted to the moving member element, were aligned with the test tape. The test tape was peeled forward by hand a distance of approximately 2.54 cm (1 in.) and the clamping fixtures were attached in order to provide a 180 degree peel angle. The test tape was then peeled at a constant peel rate until a steady force level was observed, or until it was observed that there was adhesive failure of the noble metal from the polymer (i.e., composite bond failure). The peel rate, peel force, and the observation of the absence or presence of composite bond failure were each recorded. The highest rate of peel for which composite bond failure was absent was identified. The peel force(s) measured at this highest rate of peel were then determined. An Average Peel Force ($\overline{F}$) value and a Standard Deviation ($S_F$) were calculated in a normalized form as force divided by test tape width, for each composite.

$\overline{F}$ = Average Peel Force (the average of at least two total measurements). In general, $\overline{F}=((\Sigma F_i)/n)$ in kg/mm.

$S_F$ = Standard Deviation of Peel Force (calculated from data for at least two measurements).
$S_F=(1/(n-1)\times(\Sigma(F_i-\overline{F})^2))^{\frac{1}{2}}$.

Note: $F_i$ = Individual peel force of measurement #i.

n = The number of measurements.

To evaluate the noble metal/polymer composite portion of an article such as an electrode, it is necessary to remove any coatings or passivation layers of materials covering the composite. Articles that are not in planar form can be tested by applying adhesive film (e.g., Ablefilm 550 Adhesive Film, Ablestik Laboratories, Gardena, Calif.) to each test panel using the method described above. One or more such articles can then be laid onto a test panel-adhesive film structure in a manner that corresponds with the location of a "specimen subregion", as described above.

When more than one article is to be bonded within a particular "specimen subregion", the multiple articles can be positioned in a closely packed arrangement such that no adhesive is visible between the articles. The test specimens can be heated for 2 hours at 150° F. (66° C.) with a constant 34,000 pascals (5 PSI) compressive stress applied to the specimen and allowed to cool to room temperature. An oligomeric dimethylsiloxane (e.g., #360 Medical Fluid, Dow Corning, Midland, Mich.) is applied at a thickness of about 12.7 microns (0.0005 in.), to any surface that would correspond to the location of a "specimen subregion" of each test panel except surfaces of articles to be peel tested, or surfaces located within a distance of 50 microns (0.002 in.) of articles to be peel tested. The width of the articles (or group of articles) to be peel tested is measured in several places. If the width varies more than 5%, edge portions of the article (or assemblage of articles) can be cut away so that the resultant width variation does not exceed 5% of the average width.

TEST METHOD B: SHEET RESISTANCE

The electrical resistance of the noble metal coating was evaluated in the manner described below according to ASTM Method B 539-80, as described in Maissel et.al., "Handbook of Thin Film Technology", pp. 13-5 to 13-7, McGraw-Hill Book Co. (1983), the disclosure of which is hereby incorporated by reference.

Noble metal/polymeric support composite samples were prepared as 7.62 cm×20.32 cm (3 in.×8 in.) specimens. Each specimen had at least two subregions, each of which was 2.54 cm (1.0 in.)×20.32 cm (8.0 in.) in size.

Test panels of borosilicate low-expansion glass, such as Corning 7740, available from Corning Glass Works, Corning, N.Y. were washed using detergent solution followed by rinsing with water of at least 1 Megohm-cm resistivity. The panels were then rinsed with a solution containing 70 parts heptane to 30 parts isopropanol by volume and dried for 10 minutes at 100° C. Specimens were bonded to test panels using either the adhesive portion of the specimen itself (if provided as a tape), or an adhesive prepared as follows: A liquid acrylic adhesive solution of the pressure sensitive adhesive (PSA) variety, or a solid such as acrylic pressure sensitive transfer adhesive; (e.g., Scotch brand "467MP Laminating Adhesive"(Converter Specialties Division, 3M, St. Paul, Minn.)) was uniformly applied to test panels in order to form a uniform solid coating of 25-50 microns (0.001-0.002 in.) thickness. Solvents were removed from the prepared adhesive by baking the coated panels for 2 hours at 90° C. (with protection from airborne dust contamination). In order to minimize the amount of entrapped air between the adhesive layer and the panel surface, a release liner was placed over the adhesive surface and four rolling passes (1 second/pass) were made over all parts of the release liner using a 2016-2240 gram (4.5-5.0 lb.) roller having a 9.53 cm rolling surface. The release liner was then peeled away to expose the underlaying adhesive surface.

The uncoated back portion of each specimen prepared from a polymeric film (as opposed to tape) was cleaned using a solvent solution containing 70 parts heptane to 30 parts isopropanol by volume and allowed to dry under ambient conditions for 5 minutes. Specimens were gently laid onto the adhesive surface, and a soft cotton tipped applicator was used to gently press the advancing contact line of specimen onto the adhesive surface while wiping from side to side. The resulting "sandwich" was rolled using four complete passes (1 second/pass) of a 2016-2240 gram (4.5-5.0 lb.) roller having a smooth rubber rolling surface.

A probe for measuring sheet resistance was constructed having individual, spring loaded metal contacts having curved tip surfaces (rounded to a radius of curvature of approximately 38.5 mm). The tips were constructed so as not to impart a compressive stress on the test surface in excess of 0.11 Megapascals (16 psi). This particular stress was found to be useful with all but the softest supports (e.g., films prepared from Hytrel TM resin). With soft supports it is necessary to use a probe or other technique that does not itself disrupt the coating, e.g., by deforming the underlying support as the probe is brought into contact with the surface. For specimens 2.54 cm×2.54 cm (1.0 in.×1.0 in.) or larger, a probe having 4 elements, mounted in a collinear arrangement with a probe tip to probe tip spacing distance of 0.423 cm (0.167 in.) in an electrically insulating support was used. The probe elements were each independently connected through insulated low resistance wires to a constant DC current source and voltmeter, such as Model 3478A, Hewlett Packard Co., Palo Alto, Calif., capable of providing a constant DC current of 1 milliamp and measure DC voltages in the range of 1.0 millivolt to 1 volt.

For the four element (equi-spaced and collinear) probe, the wires of the outer two probe elements were connected to the output connections of the constant DC current source. The wires of the inner two probe elements were connected to the voltage measurement input terminals of the voltmeter. The measured voltage (volts) and current (amps) values were used to determine sheet resistance ($R_s$). For such a probe $R_s = (V \times 4.532)/I$ (ohms/square).

The noble metal surface of each specimen mounted onto a test panel to form a "sandwich" was cleaned using the heptane/isopropanol solvent. The specimens and a platinum metal reference foil were dried for five to ten minutes at 100° C. in an oven. The probe tips were simultaneously brought into contact with the metal surface of a region of a specimen and the voltage drop (volts) and applied current (amps) were observed. Resistance levels on each of the two subregions on each specimen, and on the reference foil were calculated as follows:

Using six measurements for each composite specimen in units of ohms per 'square':

n = The number of measurements.
$\overline{A}$ = Average Sheet Resistance before/after exposure to boiling saline.
$\overline{A} = ((\Sigma A_i)/n)$ in ohms/square.
SA = Standard Deviation of Sheet Resistance.
SA = $(1/(n-1) \times (\Sigma(A_i - \overline{A})^2))^{\frac{1}{2}}$ in ohms/square.
Note: $A_i$ = Individual sheet resistance of measurement #i.

EXAMPLE 1

Sputter-Etching Pretreatment of a Polyimide Surface

Polyimide film ("Kapton" TM), was prepared by adhering #5413 Plastic Film tape (3M Company, St. Paul, Minn.) to an aluminum test panel. The tape has a polyimide film backing having a thickness of approximately 0.0038 cm (0.0015 in.) and a silicone adhesive layer having a thickness of approximately 0.0033 cm (0.0013 in.). The back surface of the film was cleaned by rinsing with heptane and isopropanol mixed in a 70 to 30 parts volume ratio ("heptane/isopropanol") to remove oils. The absorbed water was removed by baking in a Model 26 oven (Sigma Systems, San Diego, Calif.) at 180° C. in air in a covered holder for a period of two hours. The surface was cleaned of dust with a jet of ionized nitrogen gas and then subjected to sputter-etching.

Sputter-etching was carried out using an oxygen sputter plasma in a Randex sputtering system model 2400 radio frequency diode sputtering apparatus (Perkin Elmer Co., Palo Alto, Calif.) operated at a frequency of 13.56 MHz Samples were placed on a cathode of 1940 sq. cm. area. The chamber was first evacuated to a pressure of $8 \times 10^{-5}$ torr, then oxygen gas was introduced at a flow rate of 20 standard cubic centimeters per minute ("SCCM"). An equilibrium pressure of approximately 6 millitorr was maintained as oxygen was continuously introduced and removed from the system. The treatment lasted 5 minutes at an RF power level of 100 watts.

The pretreated, i.e., sputter-etched, surface of the polyimide was further processed by sputter deposition of pure platinum metal. Sputter deposition was performed using argon ion bombardment of a pure platinum target in the same chamber as described for sputter etching, without breaking the vacuum between the steps. The chamber was operated with a discharge power of 250 watts, provided by an RF generator tuned to a frequency of 13.56 MHz and coupled to a platinum cathode. First, the chamber was evacuated to a base pressure of one millitorr, then argon was introduced into the system at a constant rate of 30 SCCM, in order to maintain a working pressure of $6 \times 10^{-3}$ torr when balanced against the continuing operation of the vacuum system.

Specimens were positioned on an annular anode which rotated at a rate of 2.5 rotations per minute ("RPM") during sputter deposition, in a manner such that each specimen was brought directly under the target during each rotation. The noble metal target was sputtered for 5 minutes with the aperture to the specimens closed, after which the aperture was opened. Using a cathode having effective dimensions of 9.5 cm (3.75 in.)×4.45 cm (1.75 in.)×0.32 cm (⅛ in.), a platinum coating having a thickness of 3000 Å was achievable within nine hours. The thickness of the coating was estimated based on previous measurements of thickness that were made using a thickness measuring device ("Dektak II" surface profile measuring system, Veeco Instruments, Sloan Technology Inc. Santa Barbara, Calif.) and correlated with deposition time.

The resultant composite was used to fabricate an electrode as described below in EXAMPLE 2. Other composites were prepared in substantially the manner described above for the evaluation of sheet resistance and peel force. Using the above-described Test Method B, the sheet resistance prior to boiling saline for these composites was determined to be 1.42+/−0.46 ohms per square. The sheet resistance after boiling saline, was determined to be 4.7+/−1.3 ohms per square. The peel force of these composites after boiling saline, as determined by Test Method A, was found to be greater than 0.1 kg/mm.

These results indicate that the thin film of platinum sufficiently resisted the corrosive and degradative effects of boiling saline.

EXAMPLE 2

Fabrication of a One Sided Electrode Array

The platinum/polyimide composite of EXAMPLE 1 was fabricated using conventional photolithographic techniques to create a one-sided electrode array in the following manner. The composite was cleaned with heptane/isopropanol and allowed to dry at room temperature in air. The composite was baked at 85° C. in a natural atmosphere in a Model CR07-256 B/C oven (Blue M Co., Blue Island, Ill.) for 30 minutes. A positive photoresist ("AZ1370SF", Shipley Co., Newton, Mass.) was applied, at a nominal thickness of 3 microns, to the platinum surface by spin coating in an automated "Omnichuck" spin coating machine (Machine Technology, Inc., Parsippany, N.J.). This coating machine was set for a fluid ejection pressure of 2.1 to 2.5 kg/cm² (30 to 35 psi). Photoresist was applied for 3.5 seconds at 6 RPM followed by an 8 second spin at 3600 RPM to remove excess material. The photoresist was then baked in the same manner described in EXAMPLE 2 above, and then allowed to absorb water vapor under ambient conditions for 10 minutes.

The composite with photoresist applied thereon was then placed in a model 3001CHRZ Wafer Alignment system (Eaton Semiconductor Equipment, Kaspar Instruments model 3001, Sunnyvale, Calif.), and covered with a designed mask defining the conduction path geometry for the physical dimensions of a cochlea, for use as a cochlear implant. Besides the conduction paths and charge injection pads, the mask also defined alignment marks in order to allow alignment of a second masking, described below.

The composite thus held in the alignment system with the mask in place was then exposed to UV radiation in order to chemically modify the photoresist and make it vulnerable to a developing step. This exposure was carried out with a mercury arc UV lamp operated by a model 762 Intensity Control System (Optical Assoc., Santa Clara, Calif.) which provided 3.4 milliwatts/cm² at a wavelength in the range of 365 to 436 nm with an exposure duration of 35 seconds. The energy density of UV radiation under the recited conditions was at least 120 millijoules/cm².

The exposed photoresist was then developed, in order to remove the exposed material, for approximately 16 seconds in a solution consisting of 3.5 parts deionized water and 1 part "AZ351 Developer" TM developing solution (American Hoechst Co., Sommerville, N.J.). The composite article was then immediately rinsed in running deionized water until a temperature compensated conductivity monitor (Model 920-20M, Balsbaugh, Foxboro, Mass.) indicated that the water had returned to a resistivity of at least 1 Megohm-cm. The article was then dried with a stream of ionized nitrogen.

Sputter-etching with an argon plasma was then carried out to remove platinum not protected by photoresist. A radio frequency diode sputtering apparatus (Randex Model 2400, Perkin Elmer Co., Palo Alto, Calif.) was first evacuated to a pressure in the range of $8 \times 10^{-6}$ to $5 \times 10^{-5}$ torr, argon gas was introduced at a flow rate of 20 SCCM and the electrodes operated at a frequency of 13.56 MHz. An equilibrium pressure of approximately one millitorr was maintained as argon was continuously introduced and pumped through the system. 500 W power was required for this operation, with a duration of 60 to 75 minutes.

Sputter-etching with an oxygen plasma was then carried out in order to remove photoresist over the platinum conductor pathways. The radio frequency diode sputtering apparatus, operated at a frequency of 13.56 MHz, was first evacuated to a pressure of one millitorr, then oxygen gas was introduced at a flow rate of 20 SCCM. An equilibrium pressure of approximately $5 \times 10^{-3}$ torr was maintained as oxygen was continuously introduced and removed from the system. The power required for this step was 300 W, and this rate was maintained for approximately 20 minutes.

A "Pyralin solution" was mixed consisting of equal amounts of Pyralin PI-2555 TM (E.I. DuPont de Nemours, Inc., Wilmington, Del.), "AZ Thinner" (Shipley Co., Newton, Mass.), and reagent grade N-methyl-2-pyrrolidone. The composite was baked at 85° C. in air in a Model CR07-256 B/C oven (Blue M Co., Blue Island, Ill.) for 30 minutes, then spin coated with the Pyralin solution in an automated Omnichuck spin coating machine (Machine Technology, Inc., Parsippany, N.J.) set for a fluid ejection pressure of 30 to 40 psi. The fluid application time was set to 3 seconds at 6 RPM followed by an 8 second, 600 RPM spin to remove excess material. The composite was then baked at 85° C. in air in the Model CR07-256 B/C oven once again for 30 minutes, and allowed to cool in ambient conditions for at least 10 minutes, but preferably no longer than about 8 hours before beginning the next step.

The insulating pyralin layer was then removed at selected points, thereby creating "windows" through which charge could be delivered into the excitable nerve fibers of the body of a patient. To accomplish this, photoresist material was applied for a second time, in the same manner described above. Similarly, a second optical mask set to expose only the window areas to the UV irradiation step was placed, keying on the platinum metal alignment marks generated in the first masking. The composite article was then exposed to UV illumination sufficient to chemically change the unmasked areas and render them vulnerable to the developer. It was then immersed in the developer described earlier, in order to remove not only the exposed photoresist, but also the pyralin immediately below these areas. The composite was then rinsed sequentially in acetone and isopropanol to remove the unexposed photoresist. It was found that best results were achieved if the surface of the composite was kept wetted by solvent at all times during this procedure.

The impedance of the resultant electrode pads was determined in a circuit made up of the pads immersed in physiological saline and attached to an AC meter/AC power source by platinum wire. Monopolar pad impedance was determined using a low frequency impedance analyzer (model 4192A, Yokogawa-Hewlett Packard, Ltd., Tokyo, Japan) set at a stimulating voltage of 0.75 to 1.0 volt-RMS at 1000 Hz. All pads were 50 micron $\times$ 100 micron in size. The monopolar impedance was determined to be 4600 ohms $+/-$ 1000 ohms for 152 pads out of 154 produced on different arrays.

Finally, the electrodes were heated in a convection oven to render the pyralin fully imidized (i.e., "cured"). Further curing was carried out according to the manufacturer's suggestions by heating in an oven (model DC-256-C, Blue M Co., Blue Island, Ill.) for 35 minutes at 105° C., then for one hour at 310° C., after which they were slowly allowed to cool to room temperature.

Under conditions that approximate those encountered under physiological use, electrodes fabricated from composites of the present invention demonstrated desirable performance and uniformity.

EXAMPLE 3

Preparation of a Two-Sided Array

A Silastic TM brand medical grade silicone rubber sheet (Cat. Number 500-3, Dow Corning, Midland, Mich.) having a thickness of 0.025 cm (0.010 in.) was washed with a hot water rinse to remove talc. The sheet was then rinsed with high purity water and dried for 12 hours at 60° C. and under a vacuum of 38 cm (15 in.) Hg in a vacuum oven. A circular disk was cut from the sheet having a diameter of 6.6 cm (2.6 in.) and laid on a lint free surface. Lint and other particles were removed from the rubber sheet by using a mildly tacky tape such as 3M's Magic TM brand transparent tape (3M Company, St. Paul, Minn.). The rubber disk was then laid very flat on a clean, lint- and dust-free 7.62 cm (3 in.) silicon wafer having an indexing flat at one part of its edge.

3M brand "Kapton" tape (#5413, 3M Company, St. Paul, Minn.) from a 10.2 cm (4 in.) wide roll was then applied to the rubber disk with an air jet from a pen shaped probe. Using the air jet it was possible to lay the tape down very flat using appropriate force without stretching or scratching the polyimide surface.

This structure was then laid on a flat, mirror-finish stainless steel panel and placed in a hydraulic platen press (Model 12-10-2T, Wabash Metal Products Company, Wabash, Ind.) set to a heat of 100° C. A light contact force of approximately 3.45 to 6.89 bars (50 to 100 psi) was applied to improve the adhesion between the rubber and the pressure-sensitive adhesive. A Teflon TM liner was used to prevent contamination of the polyimide surface during this operation. To assure that symmetric pressing was achieved, the samples were pressed four times with the wafer rotated 90 degrees after each one minute press cycle.

Within eight hours, and preferably within one hour, the Kapton surface was washed with heptane/isopropanol and with soft paper towels to remove contaminants. The rubber/polyimide structure was then gently removed from the silicon wafer and inverted onto a new clean silicon wafer so that Kapton tape could be applied to the second side. It was found that a delay in performing this step resulted in excessive adhesion of the silicon wafer, making gentle removal impossible. The same lint removal, tape application, pressing, and cleaning steps described above were carried out to form a second side of an identical nature.

The circular edge of the three-layer structure (Kapton tape-silicone rubber-Kapton tape) was then taped down to the wafer using an annulus of the same Kapton tape cut from a wide roll. With the aid of a hand tool having a smooth rounded end surface this tape was laid down carefully so as to minimize any stretching of the structure, while obtaining as airtight a seal as possible. The photolithographic procedure for creating a single sided array as outlined in EXAMPLE 2 was then carried out on the exposed areas of the second side of the structure.

Sputter-etching and sputter-deposition procedures as described in EXAMPLE 1 were carried out on the first side of the structure, after first inverting the 3-layer structure and remounting it to the wafer with a piece of tape, and then placing tape strips on the first side at positions opposite the alignment marks located on the second side. The procedure described above and in EXAMPLE 2 was repeated on the first side of the article, except that the tape covering the alignment areas was removed at the time of spin coating photoresist onto side one. Reflected light microscopy through the translucent Kapton-silicone-Kapton silicone rubber structure allowed this masking to be aligned with the alignment marks still remaining on the face-down side. The electrode in its final dimensions was cut away from the structure with a surgical razor.

Electrodes prepared as described in this EXAMPLE have been soaked in 37° C. saline and subjected to intermittent electrical stress for months. After 600 hours, 39% of the electrodes had monopolar impedance below 1600 ohms, and 21% had impedance between 1600 and 40,000 ohms. The remaining 40% percent were damaged by residual DC current which dissolved the Pt metal. These results suggest that a periodic balanced AC electrical stress does not harm the platinum construction any more than does saline exposure alone.

EXAMPLE 4

Utility of the Electrode Array In Vivo

An electrode prepared as described in EXAMPLE 3 was used in testing an animal subject. The electrode had fourteen conduction paths forming seven channels, each having two poles. It was inserted into the cochleas of a cat in order to test its ability to deliver neural stimulation. The thresholds were somewhat high, but the neural responses elicited were quite normal.

EXAMPLE 5

Other Polymeric Supports

Various polymeric supports were pretreated by sputter-etching and then sputter deposited with platinum according to the method of the present invention, and evaluated according to Test Methods A and B.

The results in TABLE A below compare the maximum time elapsed, after samples were placed in boiling saline, before uniform loss of metal from the support was visible. Comparisons made in this manner were found to serve as a suitable pre-screening of materials (e.g., supports) and of the effectiveness of the sputter-etching and sputter-deposition procedures, in that higher values (e.g., greater than about 50 hours, and preferably greater than about 100 hours) tended to indicate which samples would perform well in terms of peel force and sheet resistance as determined by Test Methods A and B, respectively.

TABLE A also compares the samples prepared by a sputter-etching pretreatment followed by sputter deposition, according to the method of the present invention, with samples similarly sputter deposited although without such pretreatment. As can be seen, for each support other than the particular polyvinylidene fluoride sample used, at least one sample pretreated by sputter-etching exhibited a significantly longer maximum elapsed time before visible metal loss than did any sample not pretreated in this manner.

The particular supports used in TABLE A were as follows:

Polyimide: #5413 Plastic Film Tape, 3M Company, St. Paul, Minn., having a backing of DuPont Kapton TM polyimide.

Polyethylene terephthalate ("PET"): prepared internally according to standard techniques as extruded, biaxially oriented PET, having 0.3% AlSi slip agent.

"Hytrel TM ": extruded and biaxially oriented film prepared internally according to standard techniques from Hytrel 6098 TM resin (DuPont).

Polyvinylidene fluoride (PVF$_2$): prepared internally according to standard techniques as extruded, biaxially oriented PVF$_2$.

TABLE A

| Support | Maximum elapsed time (hours) | |
|---|---|---|
| | Sputter etch, Sputter-deposit | No sputter etch Only sputter-deposit |
| Polyimide: 3M-Kapton TM Tape | >300 | 45 |
| Polyethylene terephthalate | 80 | 30 |
| Hytrel 6098-oriented | >160 | 30 |
| Polyvinylidene fluoride | 16 | 14 |

The results in TABLE B below compare the peel force and sheet resistance for samples prepared in the same manner as those listed in TABLE A. As can be seen in TABLE B, samples prepared using the same polyimide, PET, and Hytrel TM 6098 films used above, each exhibited suitable peel force properties for use as composites of the present invention, whereas the particular polyvinylidene fluoride sample used was unsuitable for such use, under the preparation conditions used. These results correlate well with the maximum elapsed time determinations set forth in TABLE A.

The relatively high sheet resistance values for the Hytrel TM support are believed to be due to the soft, rubbery nature of this support. The stress of the electrical probes used according to Test Method B appeared to slightly deform the support in a manner that broke the continuity of the coating, thereby providing uncharacteristically high sheet resistance readings.

TABLE B

| Support | Peel Force (Kg/mm) after 100° C. Saline Aging | Sheet Resistance (ohms/square) | |
|---|---|---|---|
| | | Before | After |
| Polyimide: 3M-Kaptonr TM Tape | >0.1 | 1.42 +/− 0.46 | 4.7 +/− 1.3 |
| Polyethylene terephthalate | 0.1 | 1.46 +/− 0.52 | 5.2 +/− 2.8 |
| Hytrel TM 6098-oriented | >0.1 | 3.4 +/− 2.5 | 11 +/− 8 |
| Polyvinylidene fluoride | 0.05 | 1.71 +/− 0.66 | 5.2 +/− 1.3 |

EXAMPLE 6

Other Noble Metals

Specimens were prepared by sputter depositing iridium and gold, in the manner described above with respect to the sputter deposition of platinum. It was found that iridium exhibited suitable properties, while gold appeared to readily debond. It is likely that the adherence of all noble metals, including gold, could be improved by specifically optimizing the pretreatment and sputter deposition according to the teaching of this invention.

EXAMPLE 7

Other Support Shapes

As described previously, the application of this invention is not limited to planar, sheet-like support surfaces. Samples of cylindrical shapes, pretreated and sputter-deposited on their exterior surfaces, were prepared to demonstrate that embodiments analogous to wires could readily be prepared Such structures would find particular usefulness with modern connector technology and cabling for both AC and DC signal transmission.

Tube-like structures having outer diameters of $5.08 \times 10^{-2}$ cm (0.02 in.) and $1.27 \times 10^{-2}$ cm (0.005 in.) were prepared according to the methods described in EXAMPLE 1. Polyimide tubes (Micro-Bore TM) and polyimide coated flexible fused silica tubing were both obtained from Polymicro Technologies, Phoenix, Ariz.. Lengths of tubing up to 28 cm (11.0 in.) were coiled and mounted to silicon wafers covered with Kapton TM tape using two pieces of Kapton TM tape to hold each tube. All cleaning was done prior to mounting After baking 2 hours at 180° C. the specimens were exposed to ionized nitrogen prior to sputter etching and sputter deposition.

Sheet resistance of the resultant tubes could not be measured directly using the planar 4 point probe, but could be estimated by multiplying the resistance per unit length by the outer diameter. Sheet resistance was estimated to be 1.4 ohms per square for the $5.08 \times 10^{-2}$ cm (0.02 in.) diameter tube, and 1.8 ohms per square for the $1.27 \times 10^{-2}$ cm (0.005 in.) tube. Both of these values correlate well with data for similar planar composite shapes.

We claim:

1. A composite article comprising a polymeric support selected from the group consisting of a polyimide, polyethylene terephthalate, and polyester-ether block copolymer having a noble metal deposited directly onto at least one surface, wherein said deposited metal exhibits a peel force of at least about 0.05 kg per millimeter width after 24 hour boiling saline treatment.

2. A composite article according to claim 1 wherein said deposited metal is continuous and further exhibits
   (1) sheet resistance of about 3 ohms per square or less before boiling saline treatment, and
   (2) sheet resistance of about 9 ohms per square or less after 24 hour boiling saline treatment.

3. An article according to claim 1 wherein said polymeric support is polymidie.

4. An article according to claim 1 wherein said noble metal is selected from the group consisting of gold, iridium, palladium, platinum, rhodium, ruthenium, and their alloys.

5. An article according to claim 4 wherein said noble metal is platinum.

6. A multiconductor, microelectrode stimulation array fabricated from a composite article, said article comprising a polymeric support selected from the group consisting of a polymide, polyethylene terephthalate, and polyester-ether block copolymer, at least one surface of said support pretreated by sputter-etching and having a coating of a noble metal deposited thereon by sputter-deposition, wherein said coating exhibits a peel force of at least about 0.05 kg per millimeter width after 24 hour boiling saline treatment.

7. An array according to claim 6 wherein said polymeric support is polyimide.

8. An array according to claim 6 wherein said noble metal is selected from the group consisting of gold, iridium, palladium, platinum, rhodium, ruthenium, and their alloys.

9. An array according to claim 8 wherein said noble metal is platinum.

10. A composite article comprising a polymeric support selected from the group consisting of a polyimide, polyethylene terephthalate, and polyester-ether block copolymer having a coating of a noble metal deposited on at least one surface, wherein said article is prepared by a method comprising the steps of
    (a) pretreating at least one surface of said polymeric support by sputter-etching, and
    (b) sputter-depositing a noble metal on said pretreated surface in a manner that forms a coating comprising said noble metal deposited on said surface, said coating exhibiting a peel force suitable for its intended purpose.

11. A composite article according to claim 10 wherein said coating exhibits a peel force of at least about 0.05 kg per millimeter width after 24 hour boiling saline treatment.

12. A composite article according to claim 10 wherein said coating is continuous and further exhibits
    (1) sheet resistance of about 3 ohms per square or less before boiling saline treatment, and
    (2) sheet resistance of about 9 ohms per square or less after 24 hour boiling saline treatment.

13. A multicolor, microelectrode stimulation array prepared by a method comprising the steps of:
    (1) preparing a composite article comprising a polymeric support selected from the group consisting of a polyimide, polyethylene terephthalate, and polyester-ether block copolymer, at least one surface of said support pretreated by sputter-etching and having a continuous coating of a noble metal deposited thereon by sputter-deposition, and
    (2) fabricating said array from said composite article.

* * * * *